United States Patent
Taguchi et al.

(10) Patent No.: US 9,314,782 B2
(45) Date of Patent: Apr. 19, 2016

(54) BIS(TRIFLUOROMETHANESULFONYL) ETHYL-BEARING COMPOUND AND ACID CATALYST, AND METHOD FOR PREPARING SAME

(75) Inventors: Takeo Taguchi, Hachioji (JP); Hikaru Yanai, Hachioji (JP)

(73) Assignee: Central Glass Company, Limited, Ube-shi (JP)

( * ) Notice: Subject to any disclaimer, the term of this patent is extended or adjusted under 35 U.S.C. 154(b) by 94 days.

(21) Appl. No.: 13/994,520

(22) PCT Filed: Dec. 8, 2011

(86) PCT No.: PCT/JP2011/078409
§ 371 (c)(1),
(2), (4) Date: Nov. 15, 2013

(87) PCT Pub. No.: WO2012/081488
PCT Pub. Date: Jun. 21, 2012

(65) Prior Publication Data
US 2014/0066659 A1   Mar. 6, 2014

(30) Foreign Application Priority Data
Dec. 17, 2010   (JP) ................... 2010-281174

(51) Int. Cl.
| | | |
|---|---|---|
| *C07C 317/18* | (2006.01) | |
| *B01J 31/02* | (2006.01) | |
| *C07C 67/08* | (2006.01) | |
| *C07C 317/28* | (2006.01) | |
| *C07C 317/46* | (2006.01) | |
| *C07F 7/18* | (2006.01) | |
| *C07C 317/10* | (2006.01) | |

(52) U.S. Cl.
CPC .............. *B01J 31/0232* (2013.01); *B01J 31/02* (2013.01); *B01J 31/0224* (2013.01); *C07C 67/08* (2013.01); *C07C 317/10* (2013.01); *C07C 317/18* (2013.01); *C07C 317/28* (2013.01); *C07C 317/46* (2013.01); *C07F 7/18* (2013.01); *B01J 2231/32* (2013.01); *B01J 2231/326* (2013.01); *B01J 2231/4205* (2013.01); *B01J 2231/49* (2013.01); *B01J 2540/10* (2013.01); *C07C 2101/14* (2013.01)

(58) Field of Classification Search
CPC .................................................. C07C 317/18
See application file for complete search history.

(56) References Cited

U.S. PATENT DOCUMENTS

| | | |
|---|---|---|
| 3,586,616 A | 6/1971 | Kropp |
| 3,962,346 A | 6/1976 | Barber, Jr. et al. |
| 4,053,519 A | 10/1977 | Koshar et al. |
| 2010/0184930 A1 | 7/2010 | Yi et al. |
| 2011/0065857 A1 | 3/2011 | Terui et al. |
| 2011/0070544 A1 | 3/2011 | Nagamori et al. |

FOREIGN PATENT DOCUMENTS

| | | |
|---|---|---|
| CN | 101628950 A | 1/2010 |
| DE | 2 012 013 A1 | 10/1970 |
| EP | 1 344 772 A1 | 9/2003 |
| JP | 7-246338 A | 9/1995 |
| JP | 9-57110 A | 3/1997 |
| JP | 9-262479 A | 10/1997 |
| JP | 2000-219692 A | 8/2000 |
| JP | 2009-242391 A | 10/2009 |
| JP | 2010-18785 A | 1/2010 |
| JP | 2010-529268 A | 8/2010 |

(Continued)

OTHER PUBLICATIONS

Yanai et al, Chemistry—A European Journal (2011), 17(42), 11747.*

(Continued)

*Primary Examiner* — Clinton Brooks
(74) *Attorney, Agent, or Firm* — Crowell & Moring LLP

(57) ABSTRACT

A bis(trifluoromethanesulfonyl)ethyl group-bearing compound represented by the following formula [1], [2] or [3]

[1]

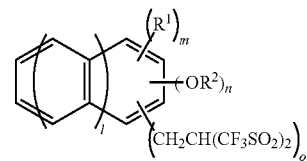

[2]

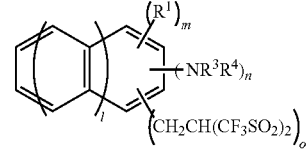

[3]

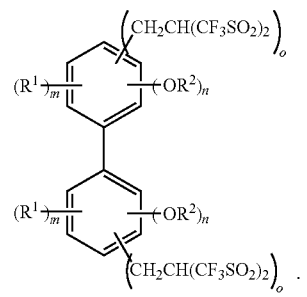

2 Claims, No Drawings

(56) References Cited

FOREIGN PATENT DOCUMENTS

WO    WO 02/48098 A1    6/2002
WO    WO 2009/151074 A1    12/2009

OTHER PUBLICATIONS

R. J Koshar et al., "Bis(perfluoroalkylsulfonyl) methanes and Related Disulfones", J. Org. Chem., vol. 38, No. 19, 1973, pp. 3358-3363.

H. Yanai et al., "Carbon Acid Induced Mukaiyama Aldol Type Reaction of Sterically Hindered Ketones", J. Org. Chem., 2010, vol. 75, pp. 5375-5378.

Corresponding International Search Report with English Translation dated Jan. 24, 2012 (four (4) pages).

"A Fluorous Super Bronsted Acid Catalyst: Application to Fluorous Catalysis without Fluorous Solvents", Ishihara et al., Graduate School of Engineering, Nagoya University, SORST, Japan Science and Technology Corporation (JST), May 9, 2002, (Five (5) pages).

* cited by examiner

BIS(TRIFLUOROMETHANESULFONYL) ETHYL-BEARING COMPOUND AND ACID CATALYST, AND METHOD FOR PREPARING SAME

TECHNICAL FIELD

The present invention relates to bis(trifluoromethanesulfonyl)ethyl group-bearing compound and acid catalyst, and a method for preparing the same.

BACKGROUND OF THE INVENTION

In the use of conventional acid catalysts exemplified by Brønsted acid such as a fuming sulfuric acid and the like or Lewis acid such as aluminium chloride, titanium tetrachloride and the like, there have been some disadvantages, for example, where a reaction is stoichiometric and a reaction solvent is limited. Hence a process for synthesis has been desired to be modified to be harmonized with the environment. The Beckmann rearrangement using a fuming sulfuric acid and the Friedel-Crafts acylation using aluminium chloride are a reaction in which a product and a catalyst form a stable additive and therefore not catalytic, so that the acid must be neutralized or decomposed to extract the product and consumed in a stoichiometric amount or more. Moreover, in the synthesis of acetophenone using benzene and acetyl chloride, a waste caused by neutralization of a waste aluminium chloride reaches 7.3 times the product.

Accordingly, the development of solid acid catalysts has become made in view of green chemistry. The solid acid catalysts are becoming used also for alkylation of aromatic compounds, though aluminium chloride has conventionally mainly been used therefor, so that most of the catalysts are replaced with zeolite catalysts (MCM-22 (MWW)) or the like in the process for synthesizing ethylbenzene or cumene. With this, a waste such as a waste catalyst, a waste salt and the like is largely reduced to solve a problem of corrosion of apparatuses and a problem of toxicity, and additionally, the continuous productivity is confirmed improved in environmental harmony and stability. Thus, advantages of solid catalysts are fully taken on a synthesis reaction of an organic compound having a commercial high temperature process-applicable and relatively simple structure. These solid acid catalysts are referred to as heterogeneous catalysts and particularly useful for synthesis of products in basic chemical industry, exhaust gas purification and the like, and therefore heavily used.

On the other hand, organic metal complexes and organic acids have been used as a catalyst in organic synthesis reactions of various conditions. These compounds having catalytic action are soluble in various organic solvents so as to be extremely useful for an organic synthesis or polymer synthesis in a liquid phase, and therefore molecules having a sulfonic acid group, such as conventionally known sulfuric acid, methanesulfonic acid and the like, have been developed as catalyst.

Of these compounds, an organic acid substituted with a trifluoromethanesulfonyl (triflyl, $CF_3SO_2$) group that exhibits a greatly strong electron-withdrawing property is known as a super strong acid of which acidity is equal to or higher than the acidity of sulfuric acid. Bis(trifluoromethanesulfonyl)methane where two triflyl groups are bonded to the same carbon and tris(trifluoromethanesulfonyl)methide where three triflyl groups are bonded to the same carbon can be cited also as an example of a compound exhibiting a strong acidity. Attempts to produce strongly acidic compounds and attempts to apply these compounds as a catalyst to synthesis reactions of pharmaceuticals, agrochemicals, polymers or an intermediate of these (e.g., Friedel-Crafts alkylation reaction, Diels-Alder reaction and the like) have hitherto been made. For example, in Patent Publication 1, there are disclosed arylbis(perfluoroalkylsulfonyl)methane, a metal salt of the same, and processes for producing these.

Moreover, in Patent Publication 2, a compound represented by the general formula $M[RfSO_2—N—SO_2Rf']_n$ or $M[RfSO_2—N—SO_2Rf']_n \cdot mH_2O$ [where each of Rf and Rf' is a $C_1$-$C_8$ perfluoroalkyl group, M is an element selected from alkali metals, alkaline earth metals, transition metals, Pb, As, Sb, Bi, Se and Te, (n) is an integer equal to the valence of a corresponding metal, and (m) is a natural number of 0.5-20.] is disclosed as a Lewis acid catalyst of which catalytic activity in an organic synthesis reaction caused by electron withdrawing reaction is increased. There are also disclosed in Patent Publication 3 organic synthesis reactions using complexes of various perfluoroalkanesulfonylimide groups and organic synthesis reactions caused by various electrophilic reactions using such complexes as catalysts.

Furthermore, in Patent Publication 4, a high activity Lewis acid catalyst usable even under coexistence of water is disclosed, the catalyst consisting of; a particular metallic halide represented by general formula $M^+(X_1^-)q$ (in the formula, M is at least one kind of metal selected from the group consisting of groups IIIA to VB elements of the periodic Table, $X_1$ is a halogen atom and (q) is an integer equal to the valence of M.); and a quaternary salt type anion exchange resin.

Additionally, in Patent Publication 5, there is disclosed an acid catalyst formed including a tris(perfluoroalkylsulfonyl) methide metal salt represented by the following formula $[(RfSO_2)_3C]_nM_2$ [where Rf is a perfluoroalkyl group having a carbon number of 1 or more, $M_2$ is an element selected from alkali metals, alkaline-earth metals, transition metals including rare earth elements, zinc, cadmium, aluminium, gallium, indium, thallium, silicon, germanium, tin, lead, arsenic, antimony, bismuth, selenium, and tellurium, and (n) is the same integer as the valence of $M_2$].

Moreover, a technique relating to the invention of the present application is disclosed in Patent Publication 6, and more specifically, 1,1,3,3-tetrakis(trifluoromethanesulfonyl) propane $((CF_3SO_2)_2CHCH_2CH(SO_2CF_3)_2$; $Tf_2CHCH_2CHTf_2)$ is disclosed as an acid catalyst useful for a carbon-carbon bond forming reaction. Additionally, Patent Publication 7 discloses a method for producing 1,1-bis(trifluoromethanesulfonyl)ethene $((CF_3SO2)_2C=CH_2)$ which is able to behave as the raw material of the propane. Furthermore, in Non-Patent Publication 1, a method for producing 1,1-bis((trifluoromethyl)sulfonyl)ethane and 1,1-bis((trifluoromethyl)sulfonyl)phenylethane is disclosed.

Incidentally, Non-Patent Publication 2 discloses various reactions for forming a carbon-carbon skeleton, in which the above-mentioned 1,1,3,3-tetrakis(trifluoromethanesulfonyl) propane is used as an acid catalyst.

REFERENCES ABOUT PRIOR ART

Patent Publication

Patent Publication 1: International Publication No. 2002-048098
Patent Publication 2: Japanese Patent Application Publication No. 7-246338
Patent Publication 3: Japanese Patent Application Publication No. 9-57110
Patent Publication 4: Japanese Patent Application Publication No. 9-262479
Patent Publication 5: Japanese Patent Application Publication No. 2000-219692
Patent Publication 6: U.S. Pat. No. 4053519
Patent Publication 7: U.S. Pat. No. 3962346

Non-Patent Publication

Non-Patent Publication 1: R. J. Koshar et al., J. Org. Chem., 38, 3358-3363 (1973)
Non-Patent Publication 2: T. Taguchi et al., J. Org. Chem., 75, 5375-5378 (2010)

SUMMARY OF THE INVENTION

Problems to be Solved by the Invention

Basically, a catalyst excellent in catalytic activity and selectivity can simplify a production process. Additionally, in industrial processes using homogeneous catalysts, the important thing is that how the catalyst degradation is controlled not only during a catalytic reaction process but also during a catalyst separation process, so it is desired to provide a novel conception of process design which improves energy efficiency even during the catalyst separation process. Synthesis reactions employing the above-mentioned organic metal complexes as a catalyst can exhibit high catalytic activity and selectivity under mild conditions, by combining a suitable central metal, ligand, reaction solvent and the like. However, the organic metal complexes are inferior to heterogeneous catalysts in heat stability, and additionally consideration must be given to controlling side reactions (such as a catalyst degradation, a demetalation, a decomposition of ligand and the like) during the catalyst separation process,; therefore, the organic metal complexes bear a disadvantage of the separation process being complicated.

An object of the present invention is to provide a carbon acid compound having a bis(trifluoromethanesulfonyl)ethyl group as acid catalysts for various organic synthesis reactions, the acid catalyst causing no reaction corrosion and being nontoxic while reducing the quantity of waste.

Means for Solving the Problems

In order to solve the above problems, the present inventors eagerly made studies. As a result, they achieved a specified bis(trifluoromethanesulfonyl)ethyl group-bearing phenolic compound.

Additionally, there was obtained an extremely useful finding that the compound can be utilized as an acid catalyst in various organic synthesis reactions such as Diels-Alder reaction, Friedel-Crafts reaction, Michael addition reaction, esterification reaction and the like.

Moreover, among these phenolic compounds, a bis(trifluoromethanesulfonyl)ethyl group-bearing compound represented by the following formula [1] was found to be an acid catalyst particularly excellent in various organic synthesis reactions

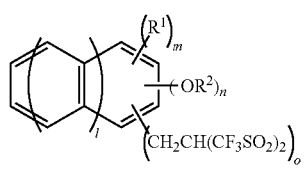
[1]

In addition, a novel finding concerning a method for producing the target phenolic compound of the present invention was obtained with relation to these findings.

More specifically, the present invention provides [Invention 1] to [Invention 8] as follows.

[Invention 1]

A bis(trifluoromethanesulfonyl)ethyl group-bearing compound represented by the following formula [1], [2] or [3].

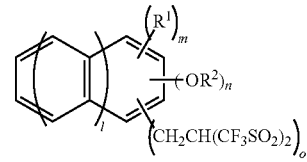
[1]

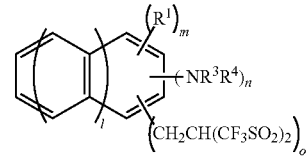
[2]

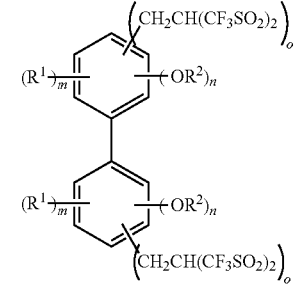
[3]

[In the formula [1], [2] or [3], $R^1$ mutually independently represents a $C_1$-$C_{12}$ straight-chain, branched or cyclic alkyl or aromatic hydrocarbon group or a halogen atom, in which the alkyl or aromatic hydrocarbon group may contain halogen (fluorine, chlorine, bromine and iodine), an oxygen atom or a carbonyl bond instead of a part of hydrogen atoms. $R^2$, $R^3$ and $R^4$ mutually independently represent a hydrogen atom or a $C_1$-$C_{12}$ straight-chain, branched or cyclic alkyl group. In the formula [1] or [2], "l" represents any integer from 0 to 2, "n" mutually independently represents any integer from 1 to 5, "m" mutually independently represents any integer from 0 to 4, "o" mutually independently represents any integer from 1 to 3, and "m+n+o≤6" is satisfied. In the formula [3], "n" mutually independently represents any integer from 1 to 5, "m" mutually independently represents any integer from 0 to 4, "o" mutually independently represents any integer from 1 to 3, and "m+n+o≤5" is satisfied. If there are two or more combinations of $R^1$ and $R^2$ or of $R^3$ and $R^4$, each combination may be either an equal one or a different one.]

[Invention 2]

A compound as discussed in Invention 1, wherein $R^1$ in the compound represented by the formula [1], [2] or [3] mutually independently represents a $C_1$-$C_6$ straight-chain or branched alkyl group, and $R^2$ mutually independently represents a hydrogen atom or a $C_1$-$C_4$ straight-chain alkyl group.

[Invention 3]

An acid catalyst comprising a bis(trifluoromethanesulfonyl)ethyl group-bearing compound represented by the following formula [1], [2] or [3].

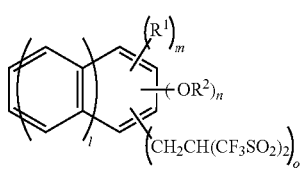

[1]

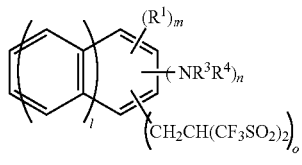

[2]

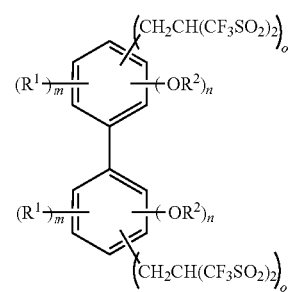

[3]

[In the formula [1], [2] or [3], R¹ mutually independently represents a $C_1$-$C_{12}$ straight-chain, branched or cyclic alkyl or aromatic hydrocarbon group or a halogen atom, in which the alkyl or aromatic hydrocarbon group may contain halogen (fluorine, chlorine, bromine and iodine), an oxygen atom or a carbonyl bond instead of a part of hydrogen atoms. R², R³ and R⁴ mutually independently represent a hydrogen atom or a $C_1$-$C_{12}$ straight-chain, branched or cyclic alkyl group. In the formula [1] or [2], "l" represents any integer from 0 to 2, "n" mutually independently represents any integer from 1 to 5, "m" mutually independently represents any integer from 0 to 4, "o" mutually independently represents any integer from 1 to 3, and "m+n+o≤6" is satisfied. In the formula [3], "n" mutually independently represents any integer from 1 to 5, "m" mutually independently represents any integer from 0 to 4, "o" mutually independently represents any integer from 1 to 3, and "m+n+o≤5" is satisfied. If there are two or more combinations of R¹ and R² or of R³ and R⁴, each combination may be either an equal one or a different one.]

[Invention 4]

An acid catalyst as discussed in Invention 3, wherein R¹ in the compound represented by the formula [1], [2] or [3] mutually independently represents a $C_1$-$C_6$ straight-chain or branched alkyl group, and R² mutually independently represents a hydrogen atom or a $C_1$-$C_4$ straight-chain alkyl group.

[Invention 5]

Use of an acid catalyst as discussed in Invention 3 or 4 in Diels-Alder reaction, aldol reaction, Friedel-Crafts reaction or esterification reaction.

[Invention 6]

A method for producing a bis(trifluoromethanesulfonyl) ethyl group-bearing compound represented by formula [1], characterized by causing 1,1,3,3-tetrakis(trifluoromethanesulfonyl)propane represented by formula [4] and a compound represented by formula [5] to react with each other.

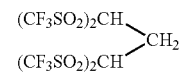

[1]

[In the formula [1], R¹, R², "l", "m" and "n" are the same as the above. "o" mutually independently represents any integer from 1 to 3, and "m+n+o≤6" is satisfied.]

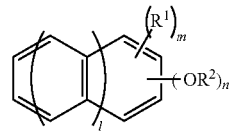

[4]

[5]

[In the formula [5], R¹ mutually independently represents a $C_1$-$C_{12}$ straight-chain, branched or cyclic alkyl or aromatic hydrocarbon group, in which the alkyl or aromatic hydrocarbon group may contain halogen (fluorine, chlorine, bromine and iodine), an oxygen atom or a carbonyl bond instead of a part of hydrogen atoms. R² mutually independently represents a hydrogen atom or a $C_1$-$C_{12}$ straight-chain, branched or cyclic alkyl group. "l" represents any integer from 0 to 2, "n" mutually independently represents any integer from 1 to 5, and "m" mutually independently represents any integer from 0 to (6-n). If there are two or more combinations of R¹ and R², each combination may be either an equal one or a different one.]

[Invention 7]

A method for producing a bis(trifluoromethanesulfonyl) ethyl group-bearing compound represented by formula [2], characterized by causing 1,1,3,3-tetrakis(trifluoromethanesulfonyl)propane represented by formula [4] and a compound represented by formula [6] to react with each other.

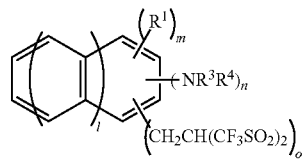

[2]

[In the formula [2], R¹, R³, R⁴, "l", "m" and "n" are the same as the above. "o" mutually independently represents any integer from 1 to 3, and "m+n+o≤6" is satisfied.]

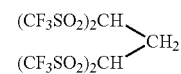

[4]

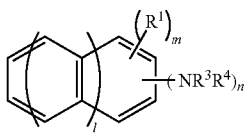

[In the formula [6], $R^1$ mutually independently represents a $C_1$-$C_{12}$ straight-chain, branched or cyclic alkyl or aromatic hydrocarbon group, in which the alkyl or aromatic hydrocarbon group may contain halogen (fluorine, chlorine, bromine and iodine), an oxygen atom or a carbonyl bond instead of a part of hydrogen atoms. $R^3$ and $R^4$ mutually independently represent a hydrogen atom or a $C_1$-$C_{12}$ straight-chain, branched or cyclic alkyl group. "l" represents any integer from 0 to 2, "n" mutually independently represents any integer from 1 to 5, and "m" mutually independently represents any integer from 0 to (6-n). If there are two or more combinations of $R^1$ and $R^2$ or of $R^3$ and $R^4$, each combination may be either an equal one or a different one.]

[Invention 8]

A method for producing a bis(trifluoromethanesulfonyl)ethyl group-bearing compound represented by formula [3], characterized by causing 1,1,3,3-tetrakis(trifluoromethanesulfonyl)propane represented by formula [4] and a compound represented by formula [7] to react with each other.

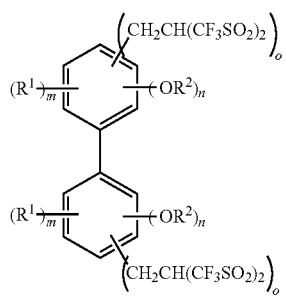

[In the formula [3], $R^1$, $R^2$, "m" and "n" are the same as the above. "o" mutually independently represents any integer from 1 to 3, and "m+n+o≤5" is satisfied.]

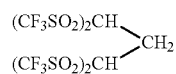

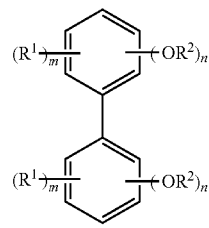

[In the formula [7], $R^1$ mutually independently represents a $C_1$-$C_{12}$ straight-chain, branched or cyclic alkyl or aromatic hydrocarbon group, in which the alkyl or aromatic hydrocarbon group may contain halogen (fluorine, chlorine, bromine and iodine), an oxygen atom or a carbonyl bond instead of a part of hydrogen atoms. $R^2$ mutually independently represents a hydrogen atom or a $C_1$-$C_{12}$ straight-chain, branched or cyclic alkyl group. "n" mutually independently represents any integer from 1 to 5, and "m" mutually independently represents any integer from 0 to (5-n). If there are two or more combinations of $R^1$ and $R^2$, each combination may be either an equal one or a different one.]

Effects of the Invention

The target compound of the invention of the present application is soluble in various solvents and therefore permits homogeneous reaction when used as an acid catalyst for various synthesis reactions. Additionally, since a moderate acidity is exhibited while a corresponding conjugated base has low nucleophilicity, a decomposition reaction of the raw material or the target compound is difficult to occur, so that the catalyst is easily and simply separated from the target compound after the reaction. In addition, the target compound of the invention of the present application can be produced even at a relatively low temperature near room temperature, thus being highly useful also in an industrial manufacturing process.

MODE(S) FOR CARRYING OUT THE INVENTION

Embodiments of the present invention will be discussed below. The present invention never be limited by the following embodiments, and may suitably be embodied within a range not to affect the scope of the present invention, on the basis of the understanding common among persons skilled in the art.

1. Compound of the Invention of the Present Application

First of all, a target compound of the present invention, i.e., a bis(trifluoromethanesulfonyl)ethyl group-bearing compound represented by formula [1], [2] or [3] will be discussed.

In the formula [1], [2] or [3], $R^1$ mutually independently represents a $C_1$-$C_{12}$ straight-chain, branched or cyclic alkyl or aromatic hydrocarbon group or a halogen atom (fluorine, chlorine, bromine and iodine).

Among examples of $R^1$, the $C_1$-$C_{12}$ straight-chain, branched or cyclic alkyl group can concretely be exemplified by methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, n-nonyl group, n-decyl group, n-dodecyl group, cyclopropyl group, cyclobutyl group, cyclopentyl group, cyclohexyl group, adamantylmethyl group and the like.

The aromatic hydrocarbon group can specifically be exemplified by phenyl group, 1-naphthyl group, 2-naphthyl group, 1-anthryl group, 1-phenanthryl group and the like.

Additionally, it is possible to substitute a part of hydrogen atoms of the alkyl or aromatic hydrocarbon group with halogen (fluorine, chlorine, bromine and iodine), an oxygen atom or a carbonyl bond.

Moreover, in the formula [1], $R^2$ mutually independently represents a hydrogen atom or a $C_1$-$C_{12}$ straight-chain, branched or cyclic alkyl group. With regard to a concrete structure of the alkyl group, the above-mentioned description (i.e., the definition of $R^1$ in the formula [1]) can be applied thereto.

Moreover, concerning definitions of $R^3$ and $R^4$ in a compound represented by the formula [2] or [3], the same definitions as the explanation on $R_2$ in the formula [1] can be applied as mentioned above.

In the formula [1] or [2], "l" represents any integer from 0 to 2, "n" mutually independently represents any integer from 1 to 5, "m" mutually independently represents any integer from 0 to 4, "o" mutually independently represents any integer from 1 to 3, and "m+n+o≤6" is satisfied.

On the other hand, "n" in the formula [3] mutually independently represents any integer from 1 to 5, "m" mutually independently represents any integer from 0 to 4, "o" mutually independently represents any integer from 1 to 3, and "m+n+o≤5" is satisfied.

In the formulas [1] to [3], substituents which will make substitution on aromatic rings (more specifically, "$(R^1)_m$", "$(OR^2)_n$", "$(NR^3R^4)_n$" and "$(CH_2CH(CF_3SO_2)_2)$") are not particularly limited in position and therefore these substituents may exist insofar as the structure is adoptable.

Compounds represented by the formulas [1] to [3] are more specifically exemplified as follows.

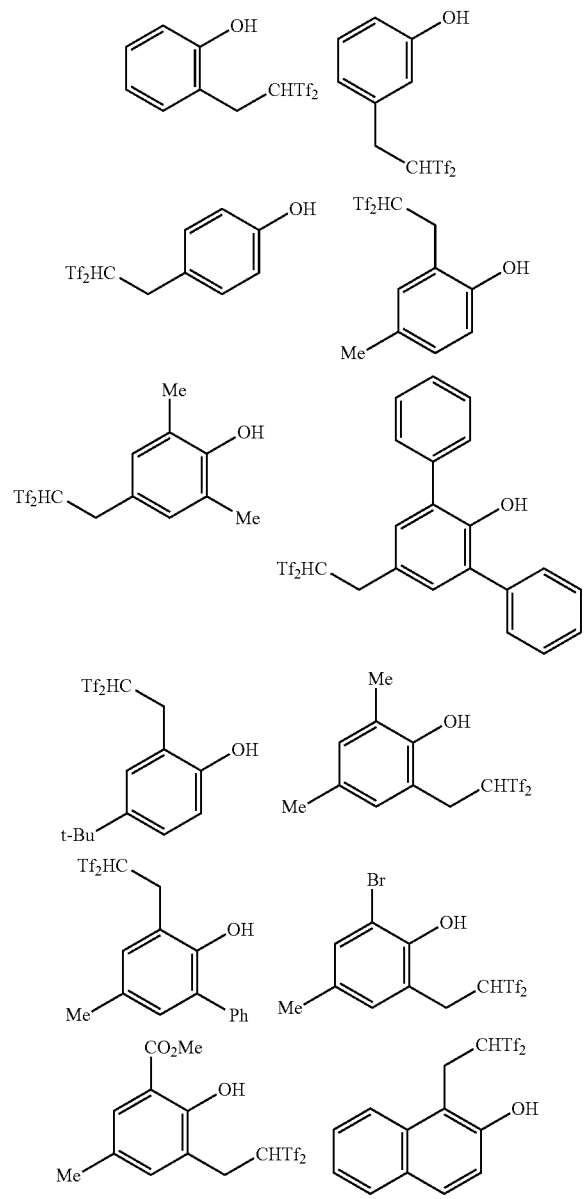

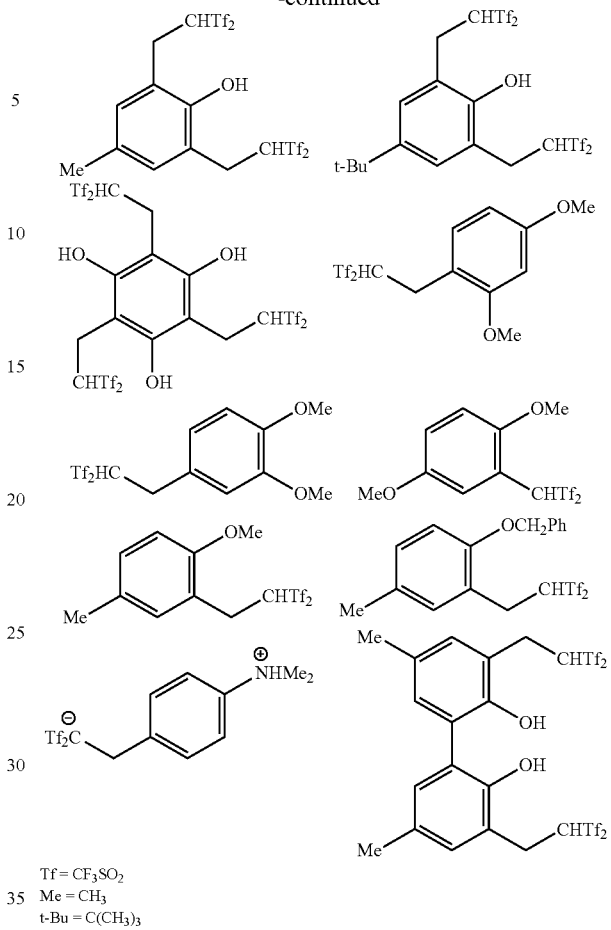

Tf = $CF_3SO_2$
Me = $CH_3$
t-Bu = $C(CH_3)_3$

Of these compounds, the structure of the following formula is obtained in such a manner that a compound represented by the formula [2] forms a salt within its molecule. In the present invention, this compound is also regarded as being included in a compound represented by the formula [2].

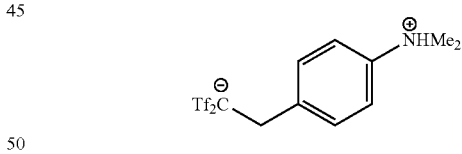

2. Use of Bis(Trifluoromethanesulfonyl)Ethyl Group-Bearing Compounds Represented by Formulas [1] to [3]

Next, the use of bis(trifluoromethanesulfonyl)ethyl group-bearing compounds represented by formulas [1] to [3] will be discussed.

Bis(trifluoromethanesulfonyl)ethyl group-bearing compounds represented by formulas [1] to [3], the target compounds of the present invention, are act as an acid catalyst in various organic synthesis reactions.

Additionally, these compounds have high activity as compared with conventionally known ones exemplified by Brønsted acid such as a fuming sulfuric acid and the like or Lewis acid such as aluminium chloride, titanium tetrachloride, boron trifluoride and the like. Furthermore, it is not necessary to use a stoichiometric amount of catalyst and therefore a desired organic reaction can proceed even when the catalyst is used in an extremely small amount. Further, a reaction solvent is not particularly limited and therefore it is possible to use general-purpose organic solvents.

The compound of the invention of the present application may be used as an acid catalyst in aldol reaction, Friedel-Crafts reaction, Diels-Alder reaction, Michael addition reaction, en reaction, esterification reaction and the like. As will be discussed in the after-mentioned examples, the following compounds selected among the compounds of the present invention exhibit particularly excellent performances when used as an acid catalyst in aldol reaction or esterification reaction.

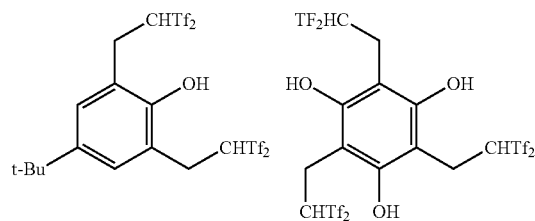

Additionally, the reaction on particular substrates proceeds with efficiency even if the amount of the catalyst is extremely small. This finding results in one preferable embodiment of the invention of the present application.

The use of an acid catalyst in various organic synthesis reactions is preferably conducted in a liquid phase reaction, similar to the cases of using usual solid catalysts. A solvent is required only not to be involved in reaction, and therefore not limited particularly; therefore, it is possible to exemplify it by saturated hydrocarbons such as n-pentane, n-hexane, n-heptane, n-octane and the like, aromatic hydrocarbons such as benzene, toluene, xylene and the like, aprotic polar solvents including ethers such as diethyl ether, tetrahydrofuran, dioxane and the like, halogenated hydrocarbons such as dichloromethane, dichloroethane, chloroform and the like, alkylketones such as acetone and the like, acetonitrile, N,N-dimethylformamide (DMF), dimethyl sulfoxide (DMSO), hexamethyl phosphoramide (HMPA) and the like.

The amount of the compound added as an acid catalyst is normally 0.001 to 10 mole times, preferably 0.01 to 5 mole times, much more preferably 0.01 to 3 mole times a reaction substrate.

Incidentally, concerning a particular acid catalyst, reduction of yield of the target reaction product was not confirmed even when the catalyst was used in an amount of 0.05 mole times a substrate (as will be discussed in the after-mentioned examples), which resulted in an industrially superior finding that a desired product can be produced with high yield.

At the time of using the compound as an acid catalyst in various organic synthesis reactions, the reaction temperature will be changed according to the amount of a reaction substrate and that of a catalyst to be added; however, the reaction is usually required only to be conducted within a range of −50 to 100° C.

A reactor is not particularly limited, and those resistant to the pressure applied during the reaction and those formed of a material not affecting the reaction are usable. The reaction may be conducted under either atmospheric pressure or an applied pressure, which may suitably adjusted by person skilled in the art according to the kind of the reaction.

Moreover, the reaction may be conducted in the flow of an inert gas such as nitrogen gas, argon gas and the like.

The reaction time is not particularly limited and usually required only to be within a range of 24 hours. It is preferable to monitor the progress of the reaction by using analysis means such as gas chromatography, liquid chromatography, NMR and the like thereby defining a point at which a substrate almost disappears as a termination.

3. Method for Producing Bis(Trifluoromethanesulfonyl) Ethyl Group-Bearing Compounds Represented by Formulas [1] to [3]

Then, a method for producing bis(trifluoromethanesulfonyl)ethyl group-bearing compounds represented by formulas [1] to [3] will be discussed.

In Patent Publication 6 as cited above, a method for causing a reaction between a bis(trifluoromethanesulfonyl)methane and paraformaldehyde thereby synthesizing 1,1,3,3-tetrakis(trifluoromethanesulfonyl)propane is disclosed (see the following scheme).

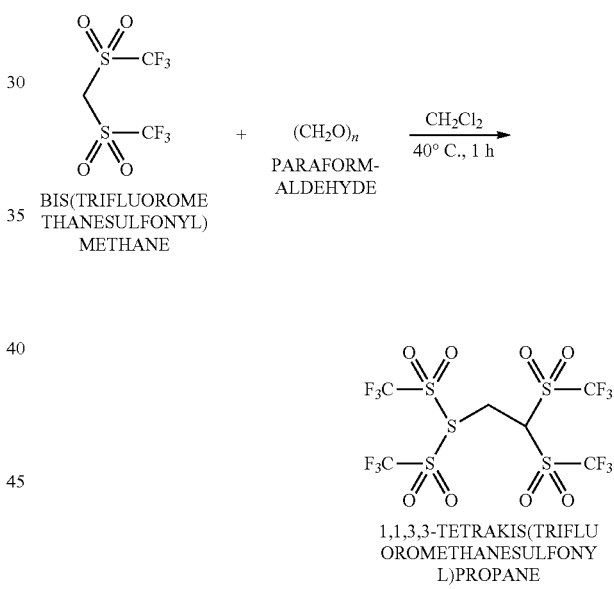

The phenolic compounds, i.e., the target compounds of the present invention represented by formulas [1] to [3] can be produced by dissolving 1,1,3,3-tetrakis(trifluoromethanesulfonyl)propane in various organic solvents at room temperature to react it with a phenolic compound that belongs to a nucleophilic species. It is conceivable that 1,1,3,3-tetrakis(trifluoromethanesulfonyl)propane is reversibly decomposed into 1,1-bis(trifluoromethanesulfonyl)ethylene and bis(trifluoromethanesulfonyl)methane in a reaction system and then the 1,1-bis(trifluoromethanesulfonyl)ethylene which serves as a highly electron-withdrawing reaction receptor reacts with a phenolic nucleophilic species thereby producing the target compound.

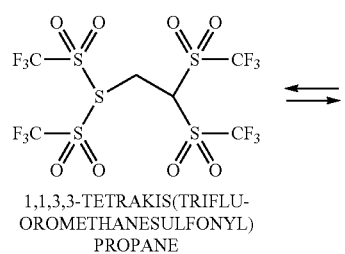 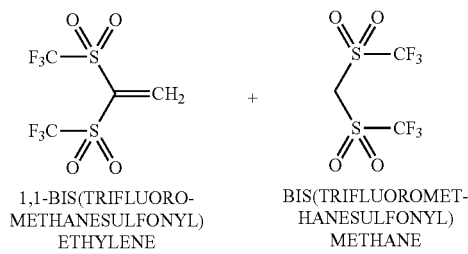

1,1,3,3-TETRAKIS(TRIFLU-OROMETHANESULFONYL)PROPANE 1,1-BIS(TRIFLUORO-METHANESULFONYL)ETHYLENE

BIS(TRIFLUOROMET-HANESULFONYL)METHANE

VARIOUS KINDS OF NUCLEOPHILIC SPECIES (PHENOLIC COMPOUND)

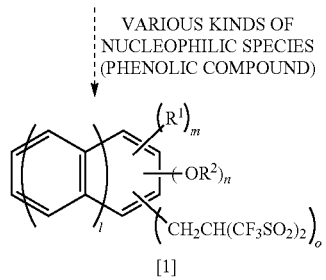

[1]

This compound may be produced in the presence of a solvent. The reaction solvent is required only not to be involved in reaction and therefore not limited particularly; therefore, it is possible to exemplify it by saturated hydrocarbons such as n-pentane, n-hexane, n-heptane, n-octane and the like, aromatic hydrocarbons such as benzene, toluene, xylene and the like, aprotic polar solvents including ethers such as diethyl ether, tetrahydrofuran, dioxane and the like, halogenated hydrocarbons such as dichloromethane, dichloroethane, chloroform and the like, alkylketones such as acetone and the like, acetonitrile, N,N-dimethylformamide (DMF), dimethyl sulfoxide (DMSO), hexamethyl phosphoramide (HMPA) and the like.

However, if a reaction material or a reaction agent is in the form of liquid at room temperature or meltable at a reaction temperature, these matters themselves will function also as a solvent. Hence it is not necessary to consciously use another solvent, which rather lightens the industrial load and economically preferable.

The reaction temperature in the method for producing the compound is normally 20 to 150° C., but it may suitably be adjusted by person skilled in the art within this temperature range according to the progress of the reaction or according to the boiling point of the reaction solvent. Incidentally, in the case of using acetonitrile as an organic solvent, it was confirmed that the reaction sufficiently progressed even caused at room temperature (about 25° C.) (see the after-mentioned examples). This is one of particularly preferable embodiments of the invention of the present application.

Furthermore, this production method was found to be able to produce the target compound even if it is a method where bis(trifluoromethanesulfonyl)methane is used as the starting material and reacted with paraformaldehyde and a phenolic compound that serves as a nucleophilic species (incidentally, such a reaction style is the so-called "one-pot reaction", and the present specification will follow this.). More specifically, it is conceivable that the reaction between bis(trifluoromethanesulfonyl)methane and paraformaldehyde forms 1,1-bis(trifluoromethanesulfonyl)ethylene in the reaction system and then it reacts with a phenolic compound thereby producing a compound represented by any of the formulas [1] to [3].

The target compound is sufficiently produced even through the one-pot reaction; however, this reaction also forms a by-product (other than the target compound, such as diarylmethane and the like) concurrently, so that the above-mentioned reaction condition using 1,1,3,3-tetrakis(trifluoromethanesulfonyl)propane is more useful for producing the target compound with high selectivity and high yield.

As to the production method of the present application, a particularly preferable finding has been obtained. More specifically, the target compound, produced by using 1,1,3,3-tetrakis(trifluoromethanesulfonyl)propane and reacting it with a phenolic compound, can be obtained at high recovery ratio when bis(trifluoromethanesulfonyl)methane formed concurrently as a by-product is separated by distillation or the like (see the after-mentioned examples). This methane may be used as a reaction agent in the one-pot reaction, or may be derivatized into 1,1,3,3-tetrakis(trifluoromethanesulfonyl) propane by using a conventionally known method. This is an extremely useful finding in view of industrial production because the by-product is so recovered as to accomplish a large reduction of waste and the by-product is reusable as the starting material.

An after-treatment method in the production method of the present invention is not particularly limited, and therefore a treatment to be conducted on the product after the termination of the reaction may be carried out according to the usual treatment for organic synthesis (e.g. recrystallization, distillation, column chromatography and the like). Though the bis(trifluoromethanesulfonyl)ethyl group-bearing compounds represented by the formulas [1] to [3] can be obtained even when the after-treatment method is added to the usual means, a distillation operation performed in this production method enables the target compound to be easily provided with high purity and yield and therefore behaves as an enormously excellent method in producing the target compound on an industrial scale.

Moreover, at the time of performing distillation, atmospheric pressure (0.1 MPa) is acceptable but a condition of reduced pressure is preferable. The material of a distillation column is not limited, so that those formed of glass, stainless steel, tetrafluoroethylene resin, chlorotrifluoroethylene resin, vinylidene fluoride resin or perfluoroalkoxy polymer resin and those produced by conducting lining on the inner surface of glass or the like may be usable. The distillation column may be charged with a filler. A distillation carried out under reduced pressures can be accomplished at relatively low temperatures, which is simple and convenient and therefore preferable.

EXAMPLES

Hereinafter the present invention will specifically be explained with reference to examples; however, the present invention is not limited by these examples. Incidentally, Me is an abbreviated symbol of a methyl group, and Tf is that of a triflyl group ($CF_3SO_2$).

[Preparation Example]

Synthesis Example of 1,1,3,3-Tetrakis(Trifluoromethylsulfonyl)Propane [4]
$Tf_2CHCH_2CHTf_2$ Paraformaldehyde (6.3 g) was stirred in methylene chloride (50 ml) while blowing nitrogen thereinto to obtain a suspension of paraformaldehyde. The suspension was added slowly to a methylene chloride (300 ml) solution of bis(trifluoromethylsulfonyl)methane (112 g, 0.4 mol) while spending 5 hours, the solution being refluxed under a nitrogen atmosphere at 40° C.

The mixture substance was stirred during 1 hour and then cooled to 15° C. thereby separating a water phase. The water phase was extracted with methylene chloride and then added to an organic phase, followed by distillation, thereby obtaining 1,1,3,3-tetrakis(trifluoromethylsulfonyl)propane [4] (100 g).

Boiling point: 92-98° C.

A higher purity of sample was obtained by recrystallization from chlorobenzene.

Melting point: 51-53° C.
Elementary analysis: $C_7H_4F_6O_8S_4$
Calculated value: 14.7% C, 39.8% F, 0.7% H
Analyzed value: 15.0% C, 39.6% F, 0.9% H Example 1

1,1,3,3-Tetrakis(trifluoromethylsulfonyl)propane [4] (121.6 mg, 0.21 mmol) was added to an acetonitrile (0.21 ml) solution of phenol (22.0 mg, 0.23 mmol) at room temperature thereby causing a reaction for 1 hour. The reaction solution was concentrated under a reduced pressure, followed by distillation purification using a Kugelrohr (180-200° C./4 mmHg) thereby obtaining a mixture of ortho and para isomers in the ratio about 2.3:1. The yield of a mixture of 2-(2,2-bis(trifluoromethylsulfonyl)ethyl)phenol [1a] and 4-(2,2-bis(trifluoromethylsulfonyl)ethyl)phenol [1b] was 72% (59.5 mg, 0.15 mmol) in total.

(ORTHO ISOMER)

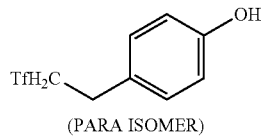

(PARA ISOMER)

Colorless liquid: IR (neat) v 3547, 3401, 2940, 1518, 1391, 1215, 1110 cm$^{-1}$. $^1$H-NMR (400 M Hz, CDCl$_3$) [1a]: δ 3.78 (2H, d, J=6.7 Hz), 5.55 (1H, S, OH), 5.87 (1H, t, J=6.7 Hz), 6.77 (1H, t, J=8.0 Hz), 6.95 (1H, t, J=8.0 Hz), 7.21-7.31 (2H, m), [1b]: δ 3.74 (2H, d, J=5.7 Hz), 5.00 (1H, t, J=5.7 Hz), 5.11 (1H, s, OH), 6.83 (2H, d, J=8.5 Hz), 7.19 (2H, d, J=8.5 Hz). $^{13}$C-NMR (100 M Hz, CDCl$_3$) [1a]: δ 28.0, 76.1, 115.1, 118.1, 119.2 (q, $J_{C-F}$=330.0 Hz), 121.6, 130.1, 132.8, 153.4, [1b]: δ 29.9, 80.1, 116.2, 119.2 (q, $J_{C-F}$=330.0 Hz), 124.9, 130.6, 155.8. $^{19}$F-NMR (282 Hz, CDCl$_3$) [1a]: δ-10.7 (6F, s), [1b]: δ-9.9 (6F, s). MS (ESI-TOF) m/z 409 [M+Na]$^+$. HRMS calcd for $C_{10}H_8F_6NaO_5S_2$ [M+Na]$^+$, 408.9615; found, 408.9566.

Example 2

1,1,3,3-Tetrakis(trifluoromethylsulfonyl)propane [4] (139.5 mg, 0.24 mmol) was added to an acetonitrile (0.25 ml) solution of p-cresol (28.1 mg, 0.27 mmol) at room temperature. After 3 hours of stirring, the reaction solution was concentrated under a reduced pressure. An obtained residue was purified by Kugelrohr distillation (180-200° C./3 mmHg) thereby obtaining 2-(2,2-bis(trifluoromethylsulfonypethyl-4-methylphenol [1c] with an approximately quantitative yield (97.0 mg, 0.24 mmol).

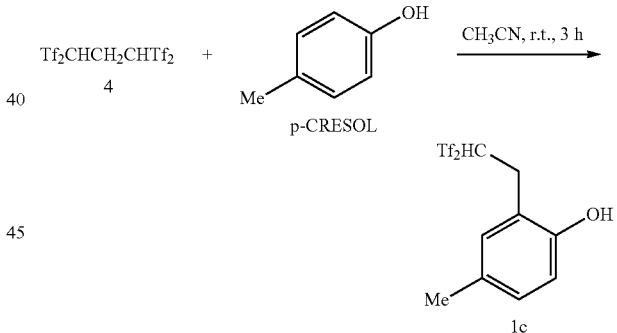

[1c]; Colorless liquid: IR (neat) v 3552, 2940, 1513, 1392, 1218, 1114, 815, 689 cm$^{-1}$. $^1$H-NMR (400 M Hz, CDCl$_3$) δ 2.27 (3H, S), 3.73 (2H, d, J=6.8 Hz), 5.36-5.52 (1H, br, OH), 5.91-5.97 (1H, m), 6.66 (1H, m), 7.03 (1H, d, J=8.1 Hz), 7.05 (1H, s). $^{13}$C-NMR (100 M Hz, CDCl$_3$) δ 20.3, 28.0, 76.0, 115.0, 117.6, 119.2 (q, $J_{C-F}$=330.0 Hz), 130.5, 130.9, 133.0, 151.2. $^{19}$F-NMR (282 Hz, CDCl$_3$) δ-10.6 (6F, s). MS (ESI-TOF) m/z 401 [M+H]$^+$. HRMS calcd for $C_{11}H_{11}F_6O_5S_2$ [M+H]$^+$, 400.9952; found, 400.9948. Anal. Calcd for $C_{11}H_{10}F_6O_5S_2$: C, 33.00; H, 2.52. Found: C, 32.82; H, 2.81.

Example 3

1,1,3,3-Tetrakis(trifluoromethylsulfonyl)propane [4] (143.2 mg, 0.25 mmol) was added to an acetonitrile (0.25 ml) solution of 2,6-xylenol (34.1 mg, 0.28 mmol) at room temperature. After 3 hours of stirring, the reaction solution was concentrated under a reduced pressure. An obtained residue was purified by Kugelrohr distillation (180-200° C./3 mmHg) thereby obtaining 4-(2,2-bis(trifluoromethylsulfonyl)ethyl-2,6-dimethylphenol [1d] with a yield of 94% (96.9 mg, 0.234 mmol). Further, recrystallization was performed thereby obtaining a colorless crystal from hexane.

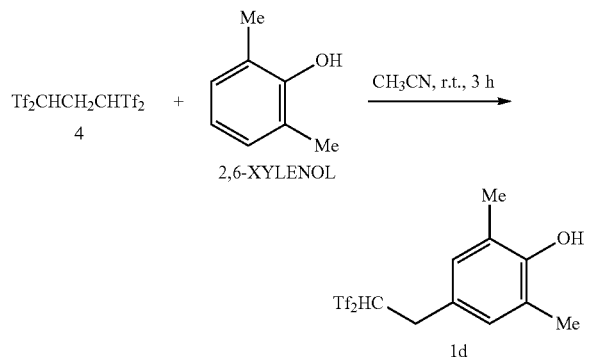

[1d]; Colorless crystal: 77.7-79.4° C. Melting point; IR (KBr) v 3585, 2932, 1492, 1393, 1208, 1109, 694 cm$^{-1}$. $^{1}$H-NMR (400 M Hz, CDCl$_3$) δ 2.23 (6H, S), 3.67 (2H, d, J=5.7 Hz), 4.76 (1H, s, OH), 5.03 (1H, t, J=5.7 Hz), 6.90 (2H, s). $^{13}$C-NMR (100 M Hz, CDCl$_3$) δ 15.8, 29.8, 80.2, 119.2 (q, $J_{C-F}$=330.0 Hz), 123.9, 124.3, 129.2, 152.3. $^{19}$F-NMR (282 Hz, CDCl$_3$) δ-9.8 (6F, s). MS (ESI-TOF) m/z 437 [M+H]$^{+}$. HRMS calcd for C$_{12}$H$_{12}$F$_6$O$_5$S$_2$ [M+Na]$^{++}$, 436.9928; found, 436.9918. Anal. Calcd for C$_{12}$H$_{12}$F6O$_5$S$_2$: C, 34.78; H, 2.92. Found: C, 35.18; H, 3.07.

Example 4

The same operations and conditions as those of Example 3 were applied with the exception that 2,4-dimethylphenol (33.6 mg, 0.275 mmol) was used instead of 2,6-xylenol. As a result, 2-(2,2-bis(trifluoromethylsulfonypethyl)ethyl-4,6-dimethylphenol [1e] was obtained with a yield of 86% (88.7 mg, 0.21 mmol). Further, recrystallization was performed thereby obtaining a colorless crystal from hexane.

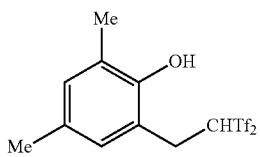

[1e]; Colorless crystal: 68.8-70.6° C. Melting point; IR (neat) v 3572, 3016, 2944, 1492, 1393, 1214, 1110, 692 cm$^{-1}$. $^{1}$H-NMR (400 M Hz, CDCl$_3$) δ 2.22 (3H, s), 2.24 (3H, s), 3.73 (2H, d, J=6.7 Hz), 4.90 (1H, s, OH), 5.88 (1H, t, J=6.7 Hz), 6.92 (1H, s), 6.93 (1H, s). $^{13}$C-NMR (100 M Hz, CDCl$_3$) δ 15.2, 20.3, 28.0, 76.3, 117.6, 119.2 (q, $J_{C-F}$=330.0 Hz), 122.2, 130.5, 130.8, 131.9, 149.5. $^{19}$F-NMR (282 Hz, CDCl$_3$) δ-10.5 (6F, s). MS (ESI-TOF) m/z 437 [M+Na]$^{+}$. HRMS calcd for C$_{12}$H$_{12}$F$_6$NaO$_5$S$_2$ [M+Na]$^{+}$, 436.9928; found, 436.9914. Anal. Calcd for C$_{12}$H$_{12}$F$_6$O$_5$S$_2$: C, 34.78; H, 2.92. Found; C, 34.87; H, 3.21.

Example 5

The same operations and conditions as those of Example 3 were applied with the exception that 2-bromo-4-methylphenol (33.2 μL, 0.275 mmol) was used instead of 2,6-xylenol and the reaction was caused at 100° C. for 10 hours. As a result, 2-(2,2-bis(trifluoromethylsulfonyl)ethyl-6-bromo-4-methylphenol [1f] was obtained with a yield of 91% (109.1 mg, 0.23 mmol).

Colorless liquid; IR (neat) v 3500, 2952, 1484, 1394, 1212, 1109 cm$^{-1}$. $^{1}$H-NMR (400 M Hz, CDCl$_3$) δ 2.27 (3H, s), 3.75 (2H, d, J=6.8 Hz), 5.79 (1H, s, OH), 5.80 (1H, t, J=6.8 Hz), 7.04 (1H, s), 7.29 (1H, s). $^{13}$C-NMR (100 M Hz, CDCl$_3$) δ 20.2, 28.4, 75.8, 109.9, 118.7, 119.2 (q, $J_{C-F}$=329.9 Hz), 132.0, 132.6, 132.7, 147.6. $^{19}$F-NMR (282 Hz, CDCl$_3$) δ-10.5 (6F, s). MS (ESI-TOF) m/z 501 [M+Na]$^{+}$, 503 [M+2+Na]$^{+}$. HRMS calcd for C$_{11}$H$_9$BrF$_6$NaO$_5$S$_2$ [M+Na]$^{+}$, 500.8877; Found, 500.8931. Anal. Calcd for C$_{11}$H$_9$BrF$_6$O$_5$S$_2$: C, 27.57; H, 1.89. Found: C, 27.85; H, 2.23.

Example 6

The same operations and conditions as those of Example 3 were applied with the exception that 2-hydroxy-5-methyl benzoate (45.7 mg, 0.275 mmol) was used instead of 2,6-xylenol and the reaction was caused at 100° C. for hours. As a result, methyl 3-(2,2-bis(trifluoromethylsulfonyl)ethyl) -2-hydroxy-5-methyl benzoate [1g] was obtained with a yield of 79% (90.6 mg, 0.20 mmol). Further, recrystallization was performed thereby obtaining a colorless crystal from hexane.

[1g]; Colorless crystal: 55.4-57.2° C. Melting point; IR (neat) v 3104, 3011, 2957, 1678, 1394, 1208, 1112, 801 cm$^{-1}$. $^{1}$H-NMR (400 M Hz, CDCl$_3$) δ 2.29 (3H, s), 3, 74 (2H, d, J=6.8 Hz), 3.96 (3H, s), 5.98 (1H, t, J=6.8 Hz), 7.30 (1H, s), 7.66 (1H, s), 11.23 (1H, s, OH). $^{13}$C-NMR (100 M Hz, CDCl$_3$) δ 20.3, 28.0, 52.6, 75.2, 112.2, 119.2 (d, $J_{C-F}$=329.9 Hz), 119.3, 129.0, 130.4, 139.2, 157.0, 170.6. $^{19}$F-NMR (282 Hz, CDCl$_3$) δ-10.6 (6F, s). MS (ESI-TOF) m/z 459 [M+H]$^{+}$. HRMS calcd for C$_{13}$H$_{13}$F$_6$O$_7$S$_2$ [M+H]$^{+}$, 459.0007; found, 459.0003.

Example 7

The same operations and conditions as those of Example 3 were applied with the exception that tert-butylphenol (49.6 mg, 0.33 mmol) was used instead of 2,6-xylenol and acetonitrile was used in an amount of 0.50 mL and the reaction was caused at 80° C. for 10 hours. As a result, 2,6-bis(2,2-bis(trifluoromethylsulfonyl)ethyl)-4-tert-butylphenol [1h] was obtained with a yield of 88% (207.3 mg, 0.28 mmol). Further, recrystallization was performed thereby obtaining a colorless crystal from hexane.

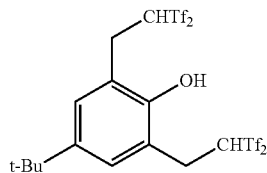

[1h]; Colorless crystal: 73.3-75.7° C. Melting point; IR (neat) v 3537, 2964, 2911, 1492, 1395, 1214, 1108 cm$^{-1}$. $^1$H-NMR (400 M Hz, CDCl$_3$-TMS) δ 1.28 (9H, s), 3.79 (4H, d, J=5.8 Hz), 5.43 (2H, t, J=5.8 Hz), 5.95 (1H, s, OH), 7.27 (2H, s). $^{13}$C-NMR (100 M Hz, CDCl$_3$) δ 27.0, 31.0, 34.3, 78.0, 119.2 (q, J$_{C-F}$=329.9 Hz), 120.8, 129.5, 146.1, 149.5. $^{19}$F-NMR (282 Hz, CDCl$_3$) δ-10.0 (12F, s). MS (ESI-TOF) m/z 757 [M+Na]$^+$. HRMS calcd for C$_{18}$H$_{18}$F$_{12}$NaO$_9$S$_4$ [M+Na]$^+$, 756.9540; Found, 756.9472. Anal. Calcd for C$_{18}$H$_{18}$F$_{12}$O$_9$S$_4$; C, 29.43; H, 2.47. Found; C, 29.56; H, 2.58.

Example 8

The same operations and conditions as those of Example 3 were applied with the exception that 1-methoxy-4-methylbenzene (34.2 mg, 0.28 mmol) was used instead of 2,6-xylenol and the reaction was caused at room temperature for 5 hours. As a result, 2-(2,2-bis(trifluoromethylsulfonyl)ethyl)-1-methoxy-4-methylbenzene [1i] was obtained with a yield of 90% (93.6 mg, 0.23 mmol). Further, recrystallization was performed thereby obtaining a colorless crystal from hexane.

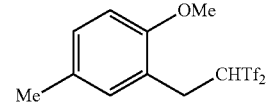

[1i]; Colorless crystal: 83.6-85.5° C. Melting point; IR (KBr) v 2959, 1383, 1216, 1196, 1134, 1033, 817 cm$^{-1}$. $^1$H-NMR (400 M Hz, CDCl$_3$) δ 2.30 (3H, s), 3.70 (2H, d, J=6.6 Hz), 3.86 (3H, s), 5.82 (1H, t, J=6.6 Hz), 6.81 (1H, d, J=8.4 Hz), 7.09 (1H, s), 7.14 (1H, d, J=8.4 Hz). $^{13}$C-NMR (100 M Hz, CDCl$_3$) δ 20.3, 28.3, 55.3, 76.0, 110.3, 119.1, 119.2 (q, J$_{C-F}$=329.9 Hz), 130.4, 130.5, 133.1, 155.0. $^{19}$F-NMR (282 Hz, CDCl$_3$) δ-10.9 (6F, s). MS (ESI-TOF) m/z 437 [M+Na]$^+$. HRMS calcd for C$_{12}$H$_{12}$F$_6$O$_5$S$_2$ [M+Na]$^+$, 436.9928; Found, 436.9950. Anal. Calcd for C$_{12}$H$_{12}$F$_6$O$_5$S$_2$: C, 34.78; H, 2.92. Found: C, 34.70; H, 3.01.

Example 9

The same operations and conditions as those of Example 3 were applied with the exception that 1-(benzyloxy)-4-methylbenzene (54.5 mg, 0.275 mmol) was used instead of 2,6-xylenol and methylene chloride (50 μL) was used instead of acetonitrile (0.25 ml) and the reaction was caused at 80° C. for 6 hours. As a result, 1-(benzyloxy)-2-(2,2-bis(trifluoromethylsulfonyl)ethyl)-4-methylbenzene [1j] was obtained with a yield of 70% (86.0 mg, 0.18 mmol). Further, recrystallization was performed thereby obtaining a colorless crystal from hexane.

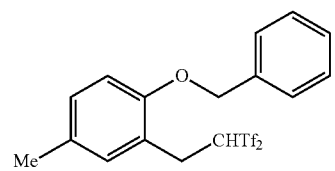

[1j]; Colorless crystal: 75.2-78.3° C. Melting point; IR (KBr) v 2948, 1391, 1221, 1118, 1009 cm$^{-1}$. $^1$H-NMR (400 M Hz, CDCl$_3$) δ 2.29 (3H, s), 3.73 (2H, d, J=7.0 Hz), 5.08 (2H, s), 5.89 (1H, t, J=7.0 Hz), 6.88 (1H, d, J=8.3 Hz), 7.10 (1H, s), 7.12 (1H, d, J=8.3 Hz), 7.33-7.45 (5H, m). $^{13}$C-NMR (100 M Hz, CDCl$_3$) δ 20.4, 28.2, 70.5, 76.0, 111.3, 118.9, 119.0 (q, J$_{C-F}$=330.2 Hz), 127.7, 128.5, 128.8, 130.4, 130.8, 133.3, 135.7, 154.4. $^{19}$F-NMR (282 Hz, CDCl$_3$) δ-10.7 (6F, s). MS (ESI-TOF) m/z 491 [M+H]$^+$. HRMS calcd for C$_{18}$H$_{17}$F$_6$O$_5$S$_2$ [M+H]$^+$, 491.0422; found, 491.0495.

Example 10

The same operations and conditions as those of Example 3 were applied with the exception that 1-(benzyloxy)-4-methylbenzene (54.5 mg, 0.275 mmol) was used instead of 2,6-xylenol and acetonitrile (0.50 mL) was used instead of acetonitrile (0.25 ml) and the reaction was caused at room temperature for 5 hours. As a result, 242,2-bis(trifluoromethylsulfonyl)ethyl)-1,4-dimethoxybenzene [1k] was obtained with a yield of 88% (94.5 mg, 0.22 mmol). Further, recrystallization was performed thereby obtaining a colorless crystal from hexane.

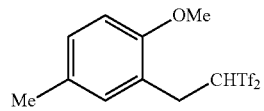

[1k]; Colorless crystal: 76.0-77.8° C. Melting point; IR (KBr) v 3026, 2974, 2940, 2845, 1376, 1235, 1193, 1122, 1026 cm$^{-1}$. $^1$H-NMR (400 M Hz, CDCl$_3$) δ 3.70 (2H, d, J=6.7 Hz), 3.77 (3H, s), 3.84 (3H, s), 5.79 (1H, t, J=6.7 Hz), 6.79-6.88 (3H, m). $^{13}$C-NMR (400 M Hz, CDCl$_3$) δ 28.5, 55.7, 55.8, 75.9, 111.2, 114.6, 118.4, 119.2 (q, J$_{C-F}$=329.9 Hz), 120.4, 151.2, 153.6. $^{19}$F-NMR (282 Hz, CDCl$_3$) δ-10.9 (6F, s). MS (ESI-TOF) m/z 431 [M+H]$^+$. HRMS calcd for C$_{12}$H$_{13}$F6O$_5$S$_2$ [M+H]$^+$, 431.0058; found, 431.0068.

Example 11

The same operations and conditions as those of Example 3 were applied with the exception that 1,2-dimethoxybenzene (34.5 mg, 0.25 mmol) was used instead of 2,6-xylenol and acetonitrile was used in an amount of 0.50 mL. As a result, 4-(2,2-bis(trifluoromethylsulfonyl)ethyl)-1,2-dimethoxybenzene [1l] was obtained with a yield of 86% (92.5 mg, 0.215 mmol). Further, recrystallization was performed thereby obtaining a colorless crystal from hexane.

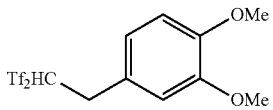

[1l]; Colorless crystal: 78.0-79.5° C. Melting point; IR (KBr) v 2943, 2843, 1519, 1391, 1215, 1110 cm$^{-1}$. $^1$H-NMR (400 M Hz, CDCl$_3$) δ 3.74 (2H, d, J=5.6 Hz), 3.87 (6H, s), 5.02 (1H, t, J=5.6 Hz), 6.81 (1H, brs), 6.83 (1H, d, J=8.1 Hz), 6.86 (1H, d, J=8.1 Hz). $^{13}$C-NMR (400 M Hz, CDCl$_3$) δ 30.2, 55.87, 55.92, 80.1, 111.5, 112.1, 119.2 (q, J$_{C-F}$=329.9 Hz), 121.4, 125.2, 149.2, 149.3. $^{19}$F-NMR (282 Hz, CDCl$_3$) δ-9.7 (6F, s). MS (ESI-TOF) m/z 431 [M+Na]$^+$. HRMS calcd for C$_{12}$H$_{13}$F$_6$NaO$_5$S$_2$ [M+H]$^+$, 431.0058; found, 431.0039.

Example 12

1,1,3,3-Tetrakis(trifluoromethylsulfonyl)propane [4] (285.8 mg, 0.50 mmol) was added to an acetonitrile (0.5 ml) solution of 2-naphthol (79.0 mg, 0.55 mmol) at room temperature. After 1 hour of stirring, recrystallization was performed thereby obtaining 1-(2,2-bis(trifluoromethylsulfonyl)ethyl)naphthalen-2-ol [1m] (a colorless crystal) from chloroform with a yield of 70% (152.7 mg, 0.35 mmol).

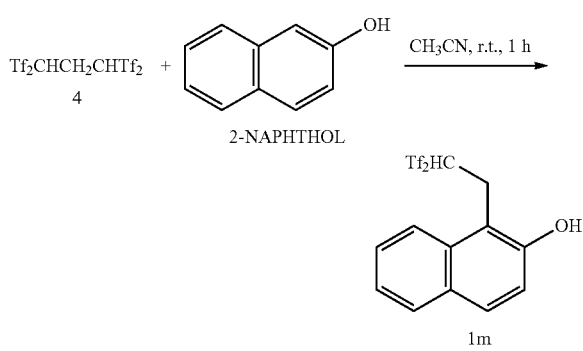

[1m]; Colorless crystal: 102.4-104.9° C. Melting point; IR (KBr) v 3544, 3068, 1361, 1585, 1391, 1216, 1109, 811, 696 cm$^{-1}$. $^1$H-NMR (400 M Hz, CDCl$_3$) δ 4.23 (2H, d, J=6.9 Hz), 5.82 (1H, s, OH), 6.14 (1H, t, J=6.9 Hz), 7.01 (1H, d, J=8.8 Hz), 7.41 (1H, dd, J=8.2, 7.2 Hz), 7.59 (1H, dd, J=8.6, 7.2 Hz), 7.78 (1H, d, J=8.8 Hz), 7.81 (1H, d, J=8.2 Hz), 8.01 (1H, d, J=8.6 Hz). $^{13}$C-NMR (100 M Hz, CDCl$_3$) δ 22.3, 75.8, 110.0, 116.7, 119.2 (q, J$_{C-F}$=330.1 Hz), 122.3, 123.9, 127.6, 128.9, 129.4, 130.9, 132.7, 151.5. $^{19}$F-NMR (282 Hz, CDCl$_3$) δ-10.6 (6F, s). MS (ESI-TOF) m/z 437 [M+H]$^+$. HRMS calcd for C$_{14}$H$_{11}$F$_6$O$_5$S$_2$ [M+H]$^+$, 436.9952; found, 436.9993.

Example 13

N,N-Dimethylaniline (22.5 µl, 0.18 mmol) in an amount of 1.0 equivalent relative to 1,1,3,3-tetrakis(trifluoromethylsulfonyl)propane [4] (101.7 mg, 0.18 mmol) was reacted in acetonitrile (0.20 ml) at 80° C. for 3 hours. Thereafter, a produced solid was filtered to be separated therefrom and then rinsed with methylene chloride (about 3 ml). It was then dried under a reduced pressure thereby obtaining a product [2a] into which a bis(trifluoromethylsulfonyl)ethyl group is introduced and a salt is formed within a molecule, with a yield of 95% (70.1 mg, 0.17 mmol). Further, recrystallization was performed thereby obtaining a colorless crystal from acetone.

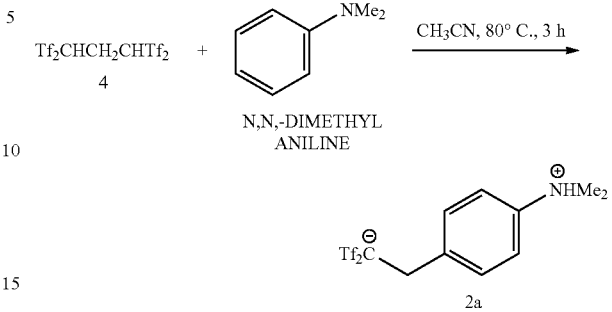

[2a]; Colorless crystal: 183.5-185.0° C. Melting point (Decomposition point); IR (KBr) v 3140, 3086, 1336, 1306, 1185, 1109, 1034 cm$^{-1}$. $^1$H-NMR (400 M Hz, CD$_3$CN) δ 3.20 (6H, s), 3.73, (2H, s), 7.44 (2H, d, J=8.7 Hz), 7.58 (2H, d, J=8.7 Hz), 8.82 (br, NH). $^{13}$C-NMR (100 M Hz, CD$_3$CN) δ 33.8, 48.0, 65.6, 120.8, 122.4 (q, J$_{C-F}$=327.9 Hz), 131.3, 140.9, 146.5. $^{19}$F-NMR (282 M Hz, CD3CN) δ-16.8 (6F, 5). MS (ESI-TOF) m/z 414 [M+H]$^+$. HRMS calcd for C$_{12}$H$_{14}$F$_6$NO$_4$S$_2$ [M+H]$^+$, 414.0268; found, 414.0280.

Example 14

1,1,3,3-Tetrakis(trifluoromethylsulfonyl)propane [4] (157.3 mg, 0.28 mmol) was added to an acetonitrile (0.25 ml) solution of 2,6-diphenylphenol (61.9 mg, 0.25 mmol) at room temperature. After 9 hours of stirring, it was purified by Kugelrohr distillation (120° C./3 mmHg) thereby obtaining 4-(2,2-bis(trifluoromethylsulfonyl)ethyl-2,6-diphenylphenol [1n] with a yield of 97% (130.7 mg, 0.24 mmol).

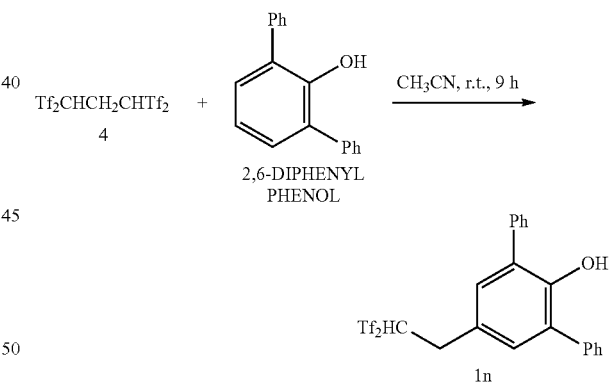

[1n]; Colorless liquid; IR (neat) v 3535, 3060, 2936, 1394, 1223, 1108, 778, 739, 700 cm$^{-1}$. $^1$H-NMR (400 M Hz, CDCl$_3$) δ 3.84 (2H, d, J=5.8 Hz), 5.12 (1H, t, J=5.8 Hz), 5.52 (1H, s, OH), 7.24 (2H, s), 7.41-7.47 (2H, m), 7.48-7.56(8H, m). $^{13}$C-NMR (100 M Hz, CDCl$_3$) δ 30.0, 80.1, 119.3 (q, J$_{C-F}$=330.2 Hz), 124.8, 128.1, 129.0, 129.2, 129.7, 130.6, 136.6, 149.6. $^{19}$F-NMR (282 Hz, CDCl$_3$) δ-9.6 (6F, s). MS (ESI-TOF) m/z 539 [M+H]$^+$. HRMS calcd for C$_{22}$H$_{16}$F$_6$O$_5$S$_2$ [M+H]$^+$, 539.0442; found, 539.0479. Anal. Calcd for C$_{22}$H$_{16}$F$_6$O$_5$S$_2$: C, 49.07; H, 2.99. Found: C, 48.74; H, 3.25.

Example 15

1,1,3,3-Tetrakis(trifluoromethylsulfonyl)propane [4] (148.8 mg, 0.264 mmol) was added to an acetonitrile (0.25 ml) solution of 4- t-butylphenol (43.6 mg, 0.29 mmol) at room temperature. After 1 hour of stirring, the reaction solution was concentrated under a reduced pressure. An obtained residue was purified by Kugelrohr distillation (190-210° C./5 mmHg) thereby obtaining 2-(2,2-bis(trifluoromethylsulfonyl)ethyl-4- t-butylphenol [1o] with an approximately quantitative yield (97.0 mg, 0.24 mmol).

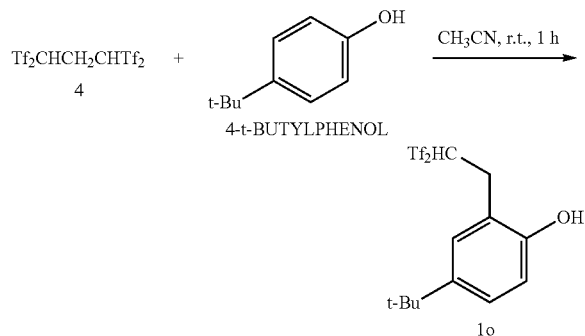

[1o]; Colorless liquid; IR (neat) v 3551, 2965, 1510, 1392, 1217, 1110, 827, 695 cm$^{-1}$. $^1$H-NMR (400 M Hz, CDCl$_3$) δ 1.28(9H, S), 3.77 (2H, d, J=6.8 Hz), 5.21-5.29 (1H, br, OH), 5.85 (1H, m), 6.89 (1H, d, J=8.4 Hz), 7.23 (1H, d, J=8.4 Hz), 7.28 (1H, s). $^{13}$C-NMR (100 M Hz, CDCl$_3$) δ 28.2, 31.1, 34.1, 76.3, 114.3, 117.2, 119.2 (q, J$_{C-F}$=330.0 Hz), 126.7, 130.1, 144.5, 151.0. $^{19}$F-NMR (282 Hz, CDCl$_3$) δ-10.6 (6F, s). MS (ESI-TOF) m/z 443 [M+H]$^+$. HRMS calcd for C$_{14}$H$_{17}$F$_6$O$_5$S$_2$ [M+H]$^+$, 443.0422; found, 443.0415. Anal. Calcd for C$_{14}$H$_{16}$F$_6$O$_5$S$_2$: C, 38.01; H, 3.65. Found: C, 37.62; H, 3.87.

Example 16

1,1,3,3-Tetrakis(trifluoromethylsulfonyl)propane [4] (113.0 mg, 0.20 mmol) was added to an acetonitrile (0.20 ml) solution of 5-methylbiphenyl-2-ol (40.0 mg, 0.22 mmol) and then stirred at 80° C. for 2 hours. The reaction solution was purified by Kugelrohr distillation (195-210° C./3 mmHg) thereby obtaining 3-(2,2-bis(trifluoromethylsulfonyl)ethyl)-5 - methylbiphenyl-2-ol [1p] with a yield of 51% (48.4 mg, 0.10 mmol).

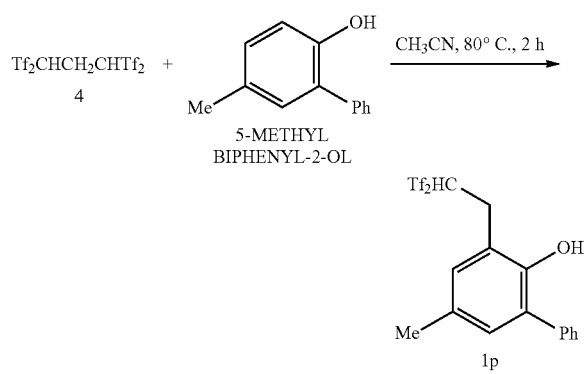

[1p]; Colorless liquid; IR (neat) v 3541, 3028, 2950, 1476, 1394, 1212, 1109, 704, 661 cm$^{-1}$. $^1$H-NMR (400 M Hz, CDCl$_3$) δ 2.32 (3H, S), 3.79 (2H, d, J=6.7 Hz), 5.52 (1H, br, OH), 5.95 (1H, t, J=6.7 Hz), 7.05 (1H, s), 7.08 (1H, s), 7.39 (2H, d, J=7.6 Hz), 7.44 (1H, t, J=7.4 Hz). $^{13}$C-NMR (100 M Hz, CDCl$_3$) δ 20.4, 28.3, 76.0, 117.6, 119.2 (q, J$_{C-F}$=330.0 Hz), 128.1, 128.5, 128.9, 129.8, 130.6, 131.1, 132.6, 135.9, 148.0. $^{19}$F-NMR (282 Hz, CDCl$_3$) δ-10.6 (6F, s). MS (ESI-TOF) m/z 499 [M+Na]$^+$. HRMS calcd for C$_{17}$H$_{14}$F$_6$O$_5$S$_2$ [M+Na]$^+$, 499.0085; found, 499.0038.

Example 17

1,1,3,3-Tetrakis(trifluoromethylsulfonyl)propane [4] (330.4 mg, 0.58 mmol) was added to an acetonitrile (0.20 ml) solution of p-cresol (21.1 mg, 0.19 mmol) and then stirred at 80° C. for 10 hours. The reaction solution was purified by Kugelrohr distillation (210-230° C./3 mmHg) thereby obtaining 2,6-bis(2,2-bis(trifluoromethylsulfonyl)ethyl)4-methylphenol [1q] with a yield of 74% (97.0 mg, 0.14 mmol).

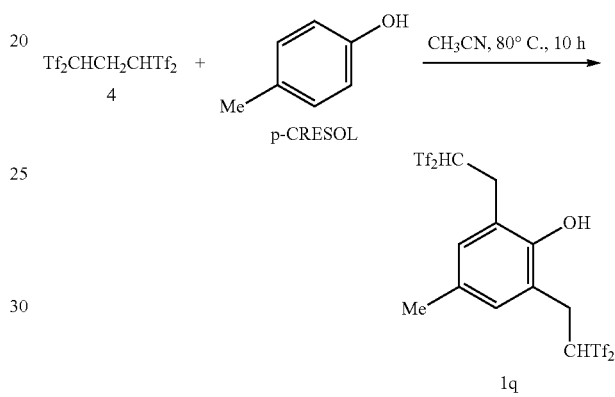

[1q]; Colorless liquid; IR (neat) v 3546, 2948, 1490, 1394, 1210, 1108, 727 cm$^{-1}$. $^1$H-NMR (400 M Hz, CDCl$_3$) δ 2.29 (3H, S), 3.75 (4H, d, J=6.2 Hz), 5.44 (1H, t, J=6.2 Hz), 5.99 (1H, s, OH), 7.06 (2H, s). $^{13}$C-NMR (100 M Hz, CDCl$_3$) δ 20.4, 26.8, 77.9, 119.2 (q, J$_{C-F}$=329.9 Hz), 121.3, 132.7, 132.8, 149.6. $^{19}$F-NMR (282 Hz, CDCl$_3$) δ-10.0(12F, s). MS (ESI-TOF) m/z 715 [M+Na]$^+$. HRMS calcd for C$_{15}$H$_{12}$F$_{12}$O$_9$S$_4$ [M+Na]$^+$, 714.9070; found, 714.9053.

Example 18

1,1,3,3-Tetrakis(trifluoromethylsulfonyl)propane [4](172.5 mg, 0.30 mmol) was added to an acetonitrile (0.50 ml) solution of 1,3-dimethoxybenzene (34.5 mg, 0.25 mmol) at room temperature. After 2 hours of stirring, the reaction solution was purified by Kugelrohr distillation (180-190° C/3mmHg) thereby obtaining 1-(2,2-bis(trifluoromethylsulfonyl)ethyl)-2,4-dimethoxybenzene [1r]with a yield of 80% (86.3 mg, 0.201 mmol). Further, recrystallization was performed thereby obtaining a colorless crystal from benzene.

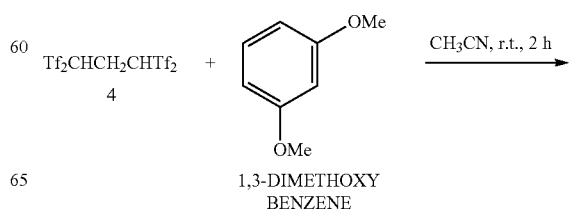

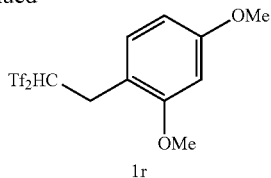

[1r]; Colorless crystal; 47.2-48.0° C. Melting point; IR (KBr) v 3009, 2948, 2843, 1617, 1510, 1392, 1211, 1115 cm$^{-1}$. $^1$H-NMR (400 M Hz, CDCl$_3$) δ 3.68 (2H, d, J=6.7 Hz), 3.81 (3H, s), 3.85 (3H, s) 5.66 (1H, t, J=6.7 Hz), 6.46 (1H, s), 6.47 (1H, d, J=8.0 Hz), 7.18 (1H, d, J=8.0 Hz). $^{13}$C-NMR (100 M Hz, CDCl$_3$) δ 27.7, 55.4 (2C), 76.1, 98.6, 104.7, 111.6, 119.2 (q, J$_{C-F}$=330.0 Hz), 133.1, 158.0, 161.5. $^{19}$F-NMR (282 Hz, CDCl$_3$) δ-10.8 (6F, s). MS (ESI-TOF) m/z 431 [M+H]$^+$. HRMS calcd for C$_{12}$H$_{13}$F$_6$O$_5$S$_2$ [M+H]$^+$, 431.0058; found, 431.0043. Anal. Calcd for C$_{12}$H$_{12}$F$_6$O$_5$S$_2$: C, 33.49; H, 2.81. Found: C, 33.39; H, 2.83.

Example 19

1,1,3,3-Tetrakis(trifluoromethylsulfonyl)propane [4] (1.89 g, 3.3 mmol) was added to an acetonitrile (1.0 ml) solution of benzene-1,3,5-triol (126 mg, 1.0 mmol) at room temperature. After 7 hours of stirring, a precipitate filtered out was rinsed with chloroform (about 5 ml). It was dried under a reduced pressure thereby obtaining 2,4,6-tris(2,2-bis(trifluoromethylsulfonyl)ethyl)benzene-1,3,5-triol [1s] with a yield of 64% (838 mg, 0.64 mmol). Further, recrystallization was performed thereby obtaining a colorless crystal from diethyl ether.

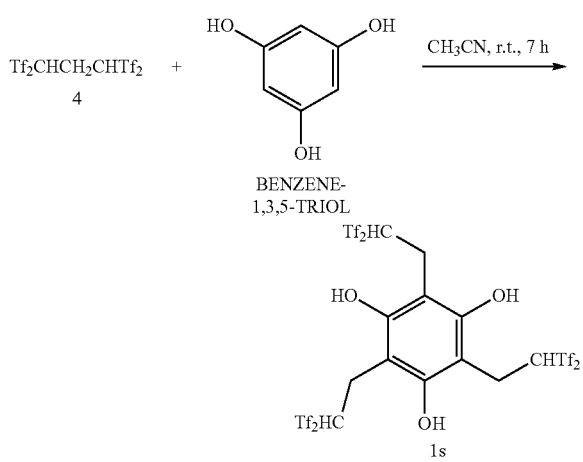

[1s]; Colorless crystal; 176.9-180.3° C. Melting point (Decomposition point); IR (neat) v 3545, 3375, 2950, 1706, 1618, 1391, 1213, 1110 cm$^{-1}$. $^1$H-NMR (400 M Hz, CD3CN) δ 3.70 (6H, d, J=6.7 Hz), 5.88 (3H, t, J=6.7 Hz), 7.29 (3H, br, OH). $^{13}$C-NMR (100 M Hz, CD$_3$CN) δ 22.2, 76.0, 101.8, 119.6 (q, J$_{C-F}$=328.9), 154.5. $^{19}$F-NMR (282 Hz, CDCl$_3$) δ-10.5 (18F, s). MS (ESI-TOF) m/z 1025 [M+Na]$^+$. HRMS calcd for C$_{18}$H$_{12}$F$_{18}$NaO$_{15}$S$_6$ [M+Na]$^+$, 1024.8111; found, 1024.8119.

Example 20

Application to Mukaiyama Aldol Reaction Catalyst

A chloroform (1.0 ml) solution of 2-TBSO-furan (specifically discussed in the following Table 1) (218 mg, 1.10 mmol) was added to a methylene chloride (1.0 ml) solution of cyclohexanone (98.0 mg, 1.00 mmol) containing a catalyst quantity of 2,4,6-tris(2,2-bis(trifluoromethylsulfonyl)ethyl)benzene-1,3,5-triol [1s] (0.5 mg, 0.5 μmol) by using a syringe pump at room temperature while spending 120 minutes. After 2 hours of stirring, a saturated aqueous solution of sodium hydrogencarbonate (20 ml) was added thereto, followed by conducting an extraction with ethyl acetate (20 ml) three times. The extracted solution was mixed with an organic phase and then dried on anhydrous magnesium sulfate. The dried matter was concentrated under a reduced pressure and purified by silica gel column chromatography (hexane: ethyl acetate=10:1 to 1:1). The obtained product has a silylated configuration [8a] and a small quantity of a desilylated configuration [8b], and in total a target aldol adduct was obtained with a yield of 77% (227.3 mg, 0.77 mmol). The ratio between silylated and desilylated configurations was about 97:3.

[8a]: $^1$H-NMR (400 M Hz, CD$_3$Cl$_3$) δ 0.12 (3H, s), 0.14 (3H, s), 0.86(9H, s), 1.25-1.74 (10H, m), 5.00-5.02 (1H, brs), 6.14 (1H, dd, J=5.8, 2.1 Hz), 7.48 (1H, dd, J=5.8, 1.5 Hz). $^{13}$C-NMR (100 M Hz, CD$_3$Cl$_3$) δ-2.2, -1.7, 18.6, 22.0 and 22.2, 25.3, 25.9, 34.4 and 35.1, 76.3, 87.9, 122.6, 154.1, 173.1.

[8b]: $^1$H-NMR (400 M Hz, CD$_3$Cl$_3$) δ 1.15-1.28 (1H, m), 1.40-1.76 (9H, m), 4.85 (1H, t, J=1.7 Hz), 6.81 (1H, dd, J=5.8, 1.7 Hz), 7.51 (1H, J=5.8, 1.7 Hz). $^{13}$C-NMR (100 M Hz, CD3Cl$_3$) δ 21.0 and 21.1, 25.4, 33.4 and 33.5, 72.6, 89.3, 122.7, 153.5, 173.0.

Example 21 to Example 26

The same procedures as those of Example 20 were repeated with the exception that 4-(2,2-bis(trifluoromethylsulfonypethyl-2,6-dimethylphenol [1d], 2-(2,2-bis(trifluoromethylsulfonynethyl-4-methylphenol [1c] or 2,6-bis(2,2-bis(trifluoromethylsulfonyl)ethyl)-4-tert-butylphenol [1h] was used and the equivalent of them was modified. Incidentally, Example 21 and Example 26 were modified such that their reaction times were 3 to 5 hours, in addition to the modification to the equivalent.

As an example for comparison (Comparative Example), the same experiment was made in the use of 1,1,3,3-tetrakis (trifluoromethanesulfonyl)propane [4]. The results of these Examples are shown in Table 1 together with the result of Example 20.

TABLE 1

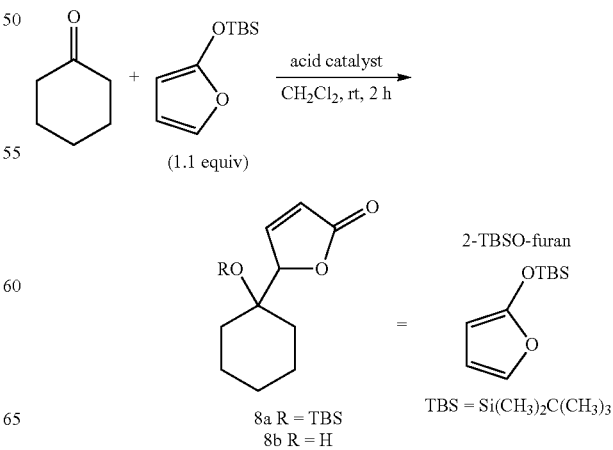

TABLE 1-continued

| TABLE 1 | ACID CATALYST (mol %) | COMBINED YIELD[a] (8A + 8B, %) |
|---|---|---|
| COMPARATIVE EXAMPLE 1[b] | Tf₂CHCH₂CHTf₂ [4] (0.5) | 82 |
| EXAMPLE 20 | [1s] (0.05) | 77 |
| EXAMPLE 21 | [1s] (0.05) | 83 |
| EXAMPLE 22 | [1s] (1.0) | 83 |
| EXAMPLE 23 | [1d] (1.0) | 30 |
| EXAMPLE 24 | [1c] (1.0) | 51 |
| EXAMPLE 25 | [1h] (1.0) | 82 |
| EXAMPLE 26 | [1h] (0.05) | 78 |

[a]Isolated yield.
[b]J. Org. Chem. 2010, 75, 5375. Reaction was carried out at −24° C.

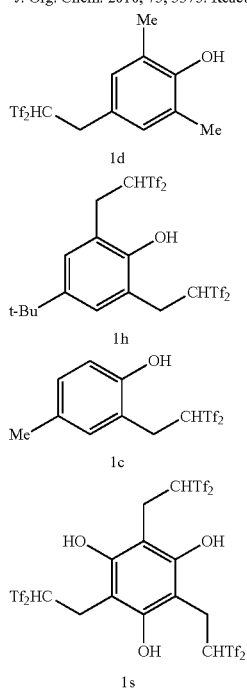

Example 27

Application to Esterification Catalyst

A mixture of (+-menthol (156 mg, 1.0 mmol), benzoic anhydride (339 mg, 1.5 mmol) and 2,4,6-tris(2,2-bis(trifluoromethylsulfonyl)ethyl)benzene-1,3,5-triol [1s] 30 mg, 30 μmol) was stirred for 3 hours at 70° C. After the reaction, a saturated aqueous solution of sodium hydrogencarbonate (10 mL) was added thereto, followed by conducting an extraction with ethyl acetate (15 mL) three times. An organic phase was rinsed with a saturated salt solution (10 mL) and then dried on anhydrous magnesium sulfate. The dried matter was concentrated under a reduced pressure and purified by silica gel column chromatography (hexane: ethyl acetate=30:1), thereby obtaining a target compound, menthyl benzoate [9], with a yield of 93% (241 mg, 0.93 mmol).

Example 28

Application to Esterification Catalyst

The same procedures as those of Example 27 were repeated with the exception that 2,6-bis(2,2-bis(trifluoromethylsulfonyl)ethyl)-4-tert-butylphenol [1h] was used instead of 2,4,6-tris(2,2-bis(trifluoromethylsulfonyl)ethyl)benzene-1,3,5-triol [1s]. As a result, a target compound menthyl benzoate [9] was obtained with a yield of 50%.

Example 27 and Example 28 are Summarized as Follows.

TABLE 2

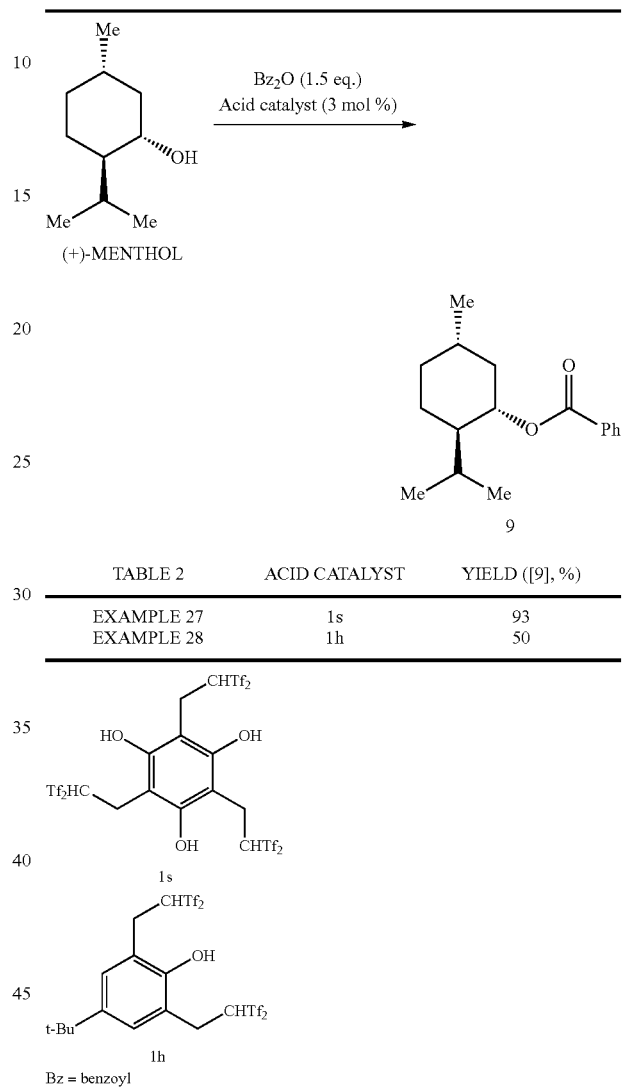

| TABLE 2 | ACID CATALYST | YIELD ([9], %) |
|---|---|---|
| EXAMPLE 27 | 1s | 93 |
| EXAMPLE 28 | 1h | 50 |

Bz = benzoyl

Example 29

Production of 2-(2,2-bis(trifluoromethylsulfonyl) ethyl-4-methylphenol [1c] and Example of Recovery of Acid Catalyst As discussed in the synthesis example of [1c] of Example 2, 1,1,3,3-Tetrakis(trifluoromethylsulfonyppropane [4] (574.4 mg, 1.00 mmol) was added to an acetonitrile (1.0 ml) solution of p-cresol (108.1 mg, 1.00 mmol) at room temperature. After 3 hours of stirring, the reaction solution was concentrated under a reduced pressure. An obtained residue was purified by Kugelrohr distillation (180-200° C./3 mmHg) thereby obtaining 2-(2,2-bis(trifluoromethylsulfonyl)ethyl-4-methylphenol [1c] with a yield of about 90% (359.4 mg, 0.90 mmol).

At this time, bis(trifluoromethanesulfonyl)methane (Tf$_2$CH$_2$) was recovered at a yield of 89% (248.4 mg, 0.89 mmol).

INDUSTRIAL APPLICABILITY

A bis(trifluoromethanesulfonyl)ethyl group-bearing compound aimed by the present invention can be utilized as an acid catalyst in various organic synthesis reactions.

The invention claimed is:

1. A method for producing a bis(trifluoromethanesulfonyl) ethyl group-bearing compound represented by formula [1], characterized by causing 1,1,3,3-tetrakis(trifluoromethanesulfonyl)propane represented by formula [4] and a compound represented by formula [5] to react with each other;

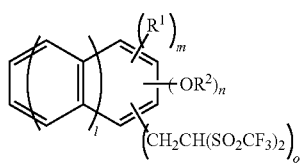

[1]

wherein in the formula [1],
R$^1$ mutually independently represents a C$_1$-C$_{12}$ straight-chain, branched or cyclic alkyl or aromatic hydrocarbon group or a halogen atom, in which the alkyl or aromatic hydrocarbon groin may contain halogen wherein the halogen is selected from the group consisting of fluorine, chlorine, bromine and iodine an oxygen atom or a carbonyl bond instead of a part of hydrogen atoms;
R$^2$ mutually independently represent a hydrogen atom or a C$_1$-C$_{12}$ straight-chain,branched or cyclic alkyl group;
"l" represents any integer from 0 to 2, "n" mutually independently represents any integer from 1 to 5, "m" mutually independently represents any integer from 0 to 4, "o" mutually independently represents any integer from 1 to 3, and m+n+o ≤6 is satisfied;

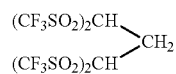

[4]

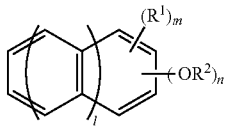

[5]

wherein in the formula [5],
R$^1$ mutually independently represents a C$_1$-C$_{12}$ straight-chain, branched or cyclic alkyl or aromatic hydrocarbon group, in which the alkyl or aromatic hydrocarbon group may contain halogen, wherein the halogen is selected from the group consisting of fluorine, chlorine, bromine and iodine, an oxygen atom or a carbonyl bond instead of a part of hydrogen atoms;
R$^2$ mutually independently represent a hydrogen atom or a C$_1$-C$_{12}$ straight-chain, branched or cyclic alkyl group;
"l" represents any integer from 0 to 2, "n" mutually independently represents any integer from 1 to 5, and "m" mutually independently represents any integer from 0 to (6-n); and wherein if there are two or more combinations of R$^1$ and R$^2$, each combination may be either an equal one or a different one.

2. A method for producing a bis(trifluoromethanesulfonyl) ethyl group-bearing compound represented by formula [2], characterized by causing 1,1,3,3-tetrakis(trifluoromehanesulfonyl)propane represented by formula [4]and a compound represented by formula [6]to react with each other

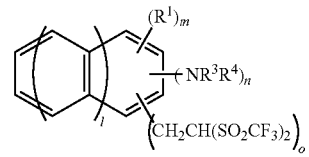

[2]

wherein in the fomula [2],
R$^1$ mutually independently represents a C$_1$-C$_{12}$ straight-chain, branched or cyclic alkyl or aromatic hydrocarbon group or a halogen atom, in which the alkyl or aromatic hydrocarbon group may contain halogen, wherein the halogen is selected from the group consisting of fluorine, chlorine, bromine and iodine an oxygen atom or carbonyl bond instead of a part of hydrogen atoms;
R$^3$ and R$^4$ mutually independently represent a hydrogen atom or a C$_1$-C$_{12}$ straight-chain, branched or cyclic alkyl group;
"1" represents any integer from 0 to 2, "n" mutually independently represents any integer from 1 to 5, "m" mutually independently represents any integer from 0 to 4, "o" mutually independently represents any integer from 1 to 3, and m+n+o≤6 is satisfied;

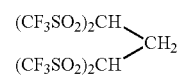

[4]

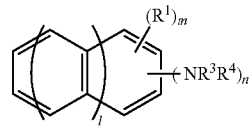

[6]

wherein in the formula [6],
R$^1$ mutually independently represents a C$_1$-C$_{12}$ straight-chain, branched or cyclic alkylor aromatic hydrocarbon group,in which the alkyl or aromatic hydrocarbon group may contain halogen, whrein the halogen is selected from the group consisting of fluorine, chlorine, bromine and idodine, an oxygen atom or carbonyl bond instead of a part of hydrogen atoms;
R$^3$ and R$^4$ mutually independently represent a hydrogen atom or a C$_1$-C$_{12}$ straight-chain, branched or cyclic alkyl group;
"1" represents any integer from 0 to 2, "n" mutually independently represents any integer from 1 to 5, and "m" mutually independently represents any integer from 0 to (6-n;)and
wherein if there are two or more combinations of R$^1$ and R$^2$ or of R$^3$ and R$^4$, each combination may be either an equal one or a different one.

* * * * *